United States Patent [19]

Bartlett et al.

[11] Patent Number: 5,268,382

[45] Date of Patent: Dec. 7, 1993

[54] MEDICAMENTS TO COMBAT AUTOIMMUNE DISEASES, IN PARTICULAR SYSTEMIC LUPUS ERYTHEMATOSUS

[75] Inventors: Robert R. Bartlett, Darmstadt; Rudolf Schleyerbach, Hofheim am Taunus; Friedrich-Johannes Kämmerer, Hochheim am Main, all of Fed. Rep. of Germany

[73] Assignee: Hoechst Aktiengesellschaft, Frankfurt am Main, Fed. Rep. of Germany

[21] Appl. No.: 870,327

[22] Filed: Apr. 17, 1992

Related U.S. Application Data

[60] Continuation of Ser. No. 575,603, Aug. 31, 1990, abandoned, which is a division of Ser. No. 911,328, Sep. 25, 1986, Pat. No. 4,965,276.

[30] Foreign Application Priority Data

Sep. 27, 1985 [DE] Fed. Rep. of Germany ....... 3534440

[51] Int. Cl.$^5$ .................... A61K 31/42; A61K 31/275
[52] U.S. Cl. ...................................... 514/378; 514/521
[58] Field of Search ............................. 514/378, 521

[56] References Cited

U.S. PATENT DOCUMENTS

| | | | |
|---|---|---|---|
| 4,284,786 | 8/1981 | Kämmerer et al. | 548/248 |
| 4,435,387 | 3/1984 | Schaub et al. | 424/180 |
| 4,435,407 | 3/1984 | Wacker | 424/263 |
| 4,965,276 | 10/1990 | Bartlett et al. | 514/378 |

OTHER PUBLICATIONS

Burling Amer Drug Int. Clin. Phar., 1988/22, 283-289.
Oxford Textbook of Medicine, Second Edition, eds. D. J. Weatherall, J. G. G. Ledingham and D. A. Warrell, vol. 2, pp. 16.20–16.28 and 21.211–21.216 (1987).

Primary Examiner—Leonard Schenkman
Attorney, Agent, or Firm—Finnegan, Henderson, Farabow, Garrett & Dunner

[57] ABSTRACT

A pharmaceutical composition for use in the treatment of chronic Graft-versus-host diseases as well as autoimmune diseases, in particular for the treatment of systemic lupus erythematosus containing as an active ingredient at least one compound of the formulae 1 or 2

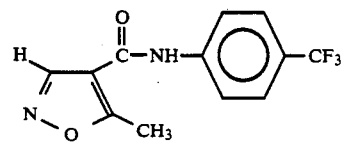

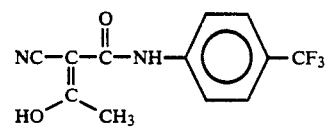

the latter being present per se or in the form of a physiologically tolerable salt.

The invention also relates to a dosage unit form of said pharmaceutical composition and a method of treating chronic Graft-versus host diseases as well as autoimmune diseases, in particular systemic lupus erythematosus.

10 Claims, 5 Drawing Sheets

MEDICAMENTS TO COMBAT AUTOIMMUNE DISEASES, IN PARTICULAR SYSTEMIC LUPUS ERYTHEMATOSUS

This application is a continuation of application Ser. No. 07/575,603, filed Aug. 31, 1990, which is a divisional of application Ser. No. 06/911,328 filed on Sep. 25, 1986 now U.S. Pat. No. 4,965,276.

The 4-trifluoromethylanilide of 5-methylisoxazole-4-carboxylic acid is known to be antiinflammatory from European Patent 13,376. This patent likewise describes processes for the preparation of this compound.

It has now been found that this compound 1 and its metabolite ⊂ N-(4-trifluoromethylphenyl)-2-cyano-3-hydroxycrotonamide (compound 2) [Stecher and Carlson, Ann. Report Med. Chem. 18, 171–179 (1983)]

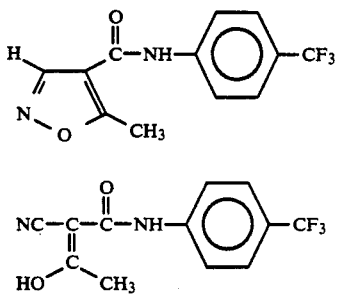

have immunomodulating properties such that they are suitable as medicaments to combat chronic graft-versus-host diseases (cGvH) and to combat autoimmune diseases, in particular systemic lupus erythematosus (SLE).

Thus the invention relates to the use of the two abovementioned compounds 1 and 2, it being possible to use compound 2 as such or in the form of a physiologically tolerated salt, for the preparation of medicaments to combat chronic graft-versus-host diseases and to combat autoimmune diseases, in particular systemic lupus erythematosus. Examples of suitable salts are alkali metal, alkaline earth metal and ammonium salts, including those of physiologically tolerated organic ammonium bases.

A) CHRONIC GRAFT-VS-HOST (cGvH) DISEASES

With transplantations there is, relatively frequently, rejection of the transplant. The transplant-host relation is, however, not confined merely to the rejection by the host organism; in certain cases there may be an immune reaction originating from the transplant and directed against the host tissue. A distinction is made between an acute and a chronic reaction. The features of the acute graft-vs.-host reaction are spleen enlargement, liver swelling, lymph node hypertrophy, hemolytic anemia, low levels of immunoglobulins and complement, and diminished immunological reactivity. The reaction which has an acute course almost always has a fatal outcome.

There is also the chronic form of the disease process. It results in lymphadenopathy, immune complex glomerulonephritis and in the formation of many antibodies. This form of the disease is milder than the acute form and does not always result in death within a short time. Symptoms produced by this cGvH reaction very closely resemble those of systemic lupus erythematosus.

B) SYSTEMIC LUPUS ERYTHEMATOSUS (SLE)

Systemic lupus erythematosus is an autoimmune disease which is not specific to any organ. This disease affects a large number of organs and has a chronic course with acute episodes. The external manifestations of SLE are lesions on the facial skin. In most cases, other areas of skin and the mucosa are affected. Also observed are nephritis, endocarditis, hemolytic anemia, leukopenia and involvement of the central nervous system.

Many immunological phenomena have been observed with SLE. There is formation of antibodies against certain endogenous antigens. These antibodies which can be detected in SLE patients are directed against, for example, the basement membrane of the skin, and against lymphocytes, erythrocytes and nuclear antigens. In the first place, the antibodies which are directed against double-stranded DNA (ds-DNA) form with the latter complexes which are deposited together with complement on small blood vessels and frequently result in vasculitis. These deposits are especially dangerous when they occur in the renal glomeruli because they result in glomerulonephritis and kidney failure. The incidence of clinically detectable involvement of the kidneys is reported in the literature to be 50 to 80%.

Glucocorticoids and other immunosuppressive medicaments, for example cyclophosphamide (CPA), are of crucial importance for the survival of patients with systemic lupus erythematosus. There is as yet no specific curative agent. To date, therapy has been aimed at preventing or overcoming acute exacerbation and averting recurrences. For this purpose, the patients have been treated with glucocorticoids and other immunosuppressants, but these themselves have hazardous side effects.

There is a variety of animal models for research into SLE. A few strains of mice spontaneously develop SLE, such as New Zealand mice or MRL/1 mice, which are animals which originated from the Jackson Laboratories, Maine, U.S.A., and which have been reared further in our own animal rooms under specific pathogen-free. (SPF) conditions. However, it is also possible to induce a disease resembling SLE by an experimental operation on non-autoimmune mice.

In the text which follows the quantities stated in mg/kg relate to kg of body weight; CMC denotes the sodium salt of carboxymethylcellulose, and N.S. denotes "no test substance". The active substances were administered orally in a mixture with CMC.

C) PHARMACOLOGICAL TESTS AND RESULTS

1) Chronic graft-vs.-host disease

Figure 1:
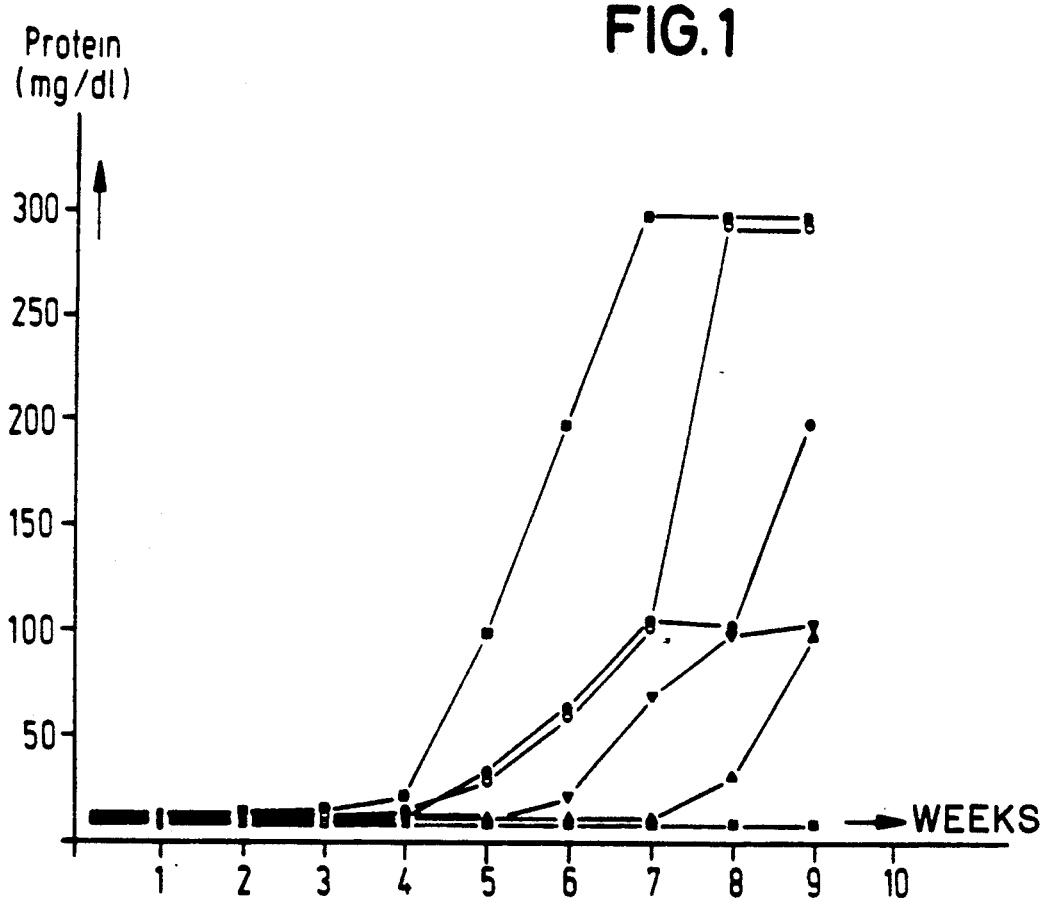
FIGS. 1–3. Amount of protein in the urine of animals established each week.

This model has been described in various publications by GLEICHMANN et al. SLE is induced by initiating a GvH reaction by an abnormal T/B-cell cooperation [GLEICHMANN et al., Euro. J. Immunol. 12; 152-159 (1982)]. The cGvH disease was initiated by two injections of spleen and thymus cells. The mice, F1 generation in accordance with GLEICHMANN et al. (DBA/2×C57Bl/6), each received $70 \times 10^6$ DBA/2 cells, injected intravenously in 0.2 ml of culture medium, on day 1 and day 8. The animals were treated for the first time on the 17th day after the first injection of the donor cells. Three independent experiments 1.1 to 1.3 were carried out, use being made in all three experiments of only female animals as donors and recipients. Each animal received oral administration of 1 ml which in each case contained the amount of active compound indicated in experiments 1.1 to 1.3, plus CMC in a concentration of 100 mg/l.

EXPERIMENTS 1.1) From day 17 onwards, the following were administered once a day:
CMC, N.S.
8 mg/kg CPA or
5 mg/kg compound 1 or
10 mg/kg compound 1 or
20 mg/kg compound 1.

There were 10 animals in each negative control group (animals without cGvH), and there were 18 animals in each of the other groups.

1.2) From day 17 onwards, the following were administered:
CMC, N.S., twice a week,
28 mg/kg compound 1 once a day or
14 mg/kg CPA twice a week or
28 mg/kg CPA twice a week or
50 mg/kg CPA twice a week.

There were 20-21 animals in each cGvH group, and there were 9 animals in each negative control group.

1.3) From day 17 onwards, the following were administered once a day:
CMC, N.S.,
1 mg/kg indomethacin or
2 mg/kg prednisolone or
20 mg/kg compound 2 or
30 mg/kg compound 2.

There were 10-11 animals in each group.

a) Proteinuria

Figure 2:
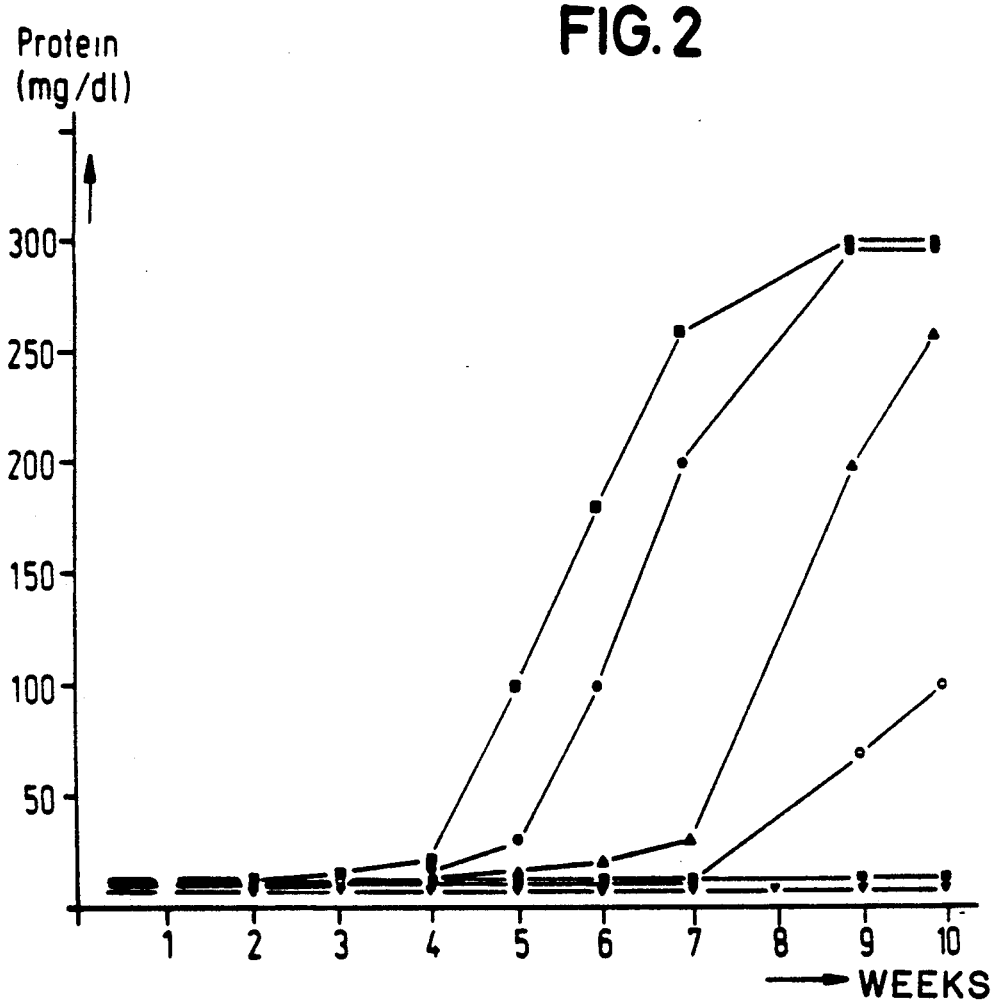
Figure 3:
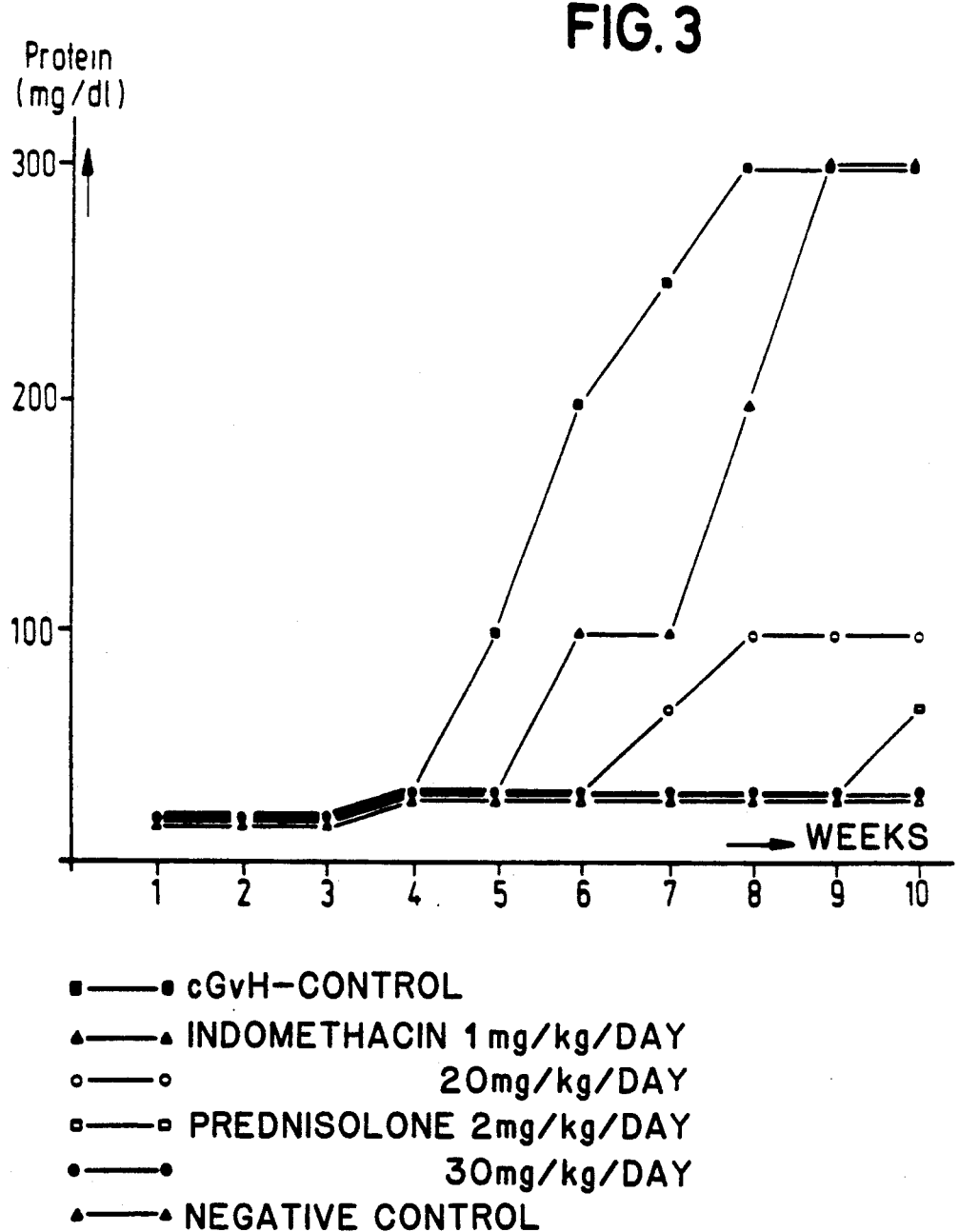

For the duration of the experiment (9-10 weeks) the amount of protein in the urine of the animals was established each week (Albu-sticks reagent sticks, Ames Division, Miles Laboratories, Elkhard). The results of these tests are shown in FIGS. 1-3.

b) Glomerulonephritis—histological tests

The proteinuria is a consequence of the damage to the nephrons by deposits of immune complexes on the basement membrane of the glomeruli. In order to establish the extent to which administration of the substance inhibits these deposits, the kidneys were removed and thin sections were prepared (10 per kidney). After the sections had been fixed and dried, they were incubated with rabbit anti-mouse immunoglobul in G (IgG). They were then washed and incubated with fluorescence-labeled pig anti-rabbit IgG. After this incubation they were washed once more, embedded and examined under a Leitz fluorescence microscope to establish the number of fluorescent glomeruli. The results of these tests are shown in Table 1.

TABLE 1

Deposition of immune complexes on the basement membrane of the glomeruli

| Experiment | Substance | Fluorescent glomeruli % | Inhibition % |
|---|---|---|---|
| 1.1 | CMC, N.S. | 100 | 0 |
| 1.1 | 8 mg/kg CPA each day | 95 | 5 |
| 1.1 | 5 mg/kg compound 1 each day | 96 | 4 |
| 1.1 | 10 mg/kg compound 1 each day | 100 | 0 |
| 1.1 | 20 mg/kg compound 1 each day | 72 | 28 |
| 1.2 | CMC, N.S. | 100 | 0 |
| 1.2 | 28 mg/kg compound 1 each day | 8 | 92 |
| 1.2 | 14 mg/kg CPA 2 × a week | 96 | 4 |
| 1.2 | 28 mg/kg CPA 2 × a week | 30 | 70 |
| 1.2 | 50 mg/kg CPA 2 × a week | 0 | 100 | c) Inhibition of the graft-vs.-host index

During the course of cGvH disease there is a considerable enlargement of the spleen as a consequence of the immunological defensive activity. If the weight of the spleen is related to the body weight of the diseased animal, and this ratio is compared with the corresponding ratio for the healthy animal, the result is the graft-vs.-host index:

$$GvH \text{ index} = \frac{\text{spleen weight } X/\text{body weight } X}{\text{spleen weight } h/\text{body weight } h}$$

where X=(diseased) animal investigated, and h=healthy animal.

It is possible with the GvH index to establish the severity of the disease: the larger the index the greater the severity of the disease. The results are shown in Table 2.

TABLE 2

| Experiment | Substance | GvH index | % change |
|---|---|---|---|
| 1.1 | CMC, N.S. | 2.06 | 0 |
| 1.1 | 8 mg/kg CPA per day | 1.03 | −50.0 |
| 1.1 | 5 mg/kg compound 1 per day | 2.00 | −2.9 |
| 1.1 | 10 mg/kg compound 1 per day | 1.97 | −4.4 |
| 1.1 | 20 mg/kg compound 1 per day | 1.67 | −19.9 |
| 1.2 | CMC, N.S. | 2.66 | 0 |
| 1.2 | 28 mg/kg compound 1 per day | 1.37 | −48.5 |
| 1.2 | 14 mg/kg CPA 2 × a week | 1.39 | −47.7 |
| 1.2 | 28 mg/kg CPA 2 × a week | 1.29 | −51.5 |
| 1.2 | 50 mg/kg CPA 2 × a week | 1.21 | −54.5 |
| 1.3 | CMC, N.S. | 2.99 | 0 |
| 1.3 | 1 mg/kg indomethacin per day | 3.44 | 115 |
| 1.3 | 2 mg/kg prednisolone per day | 1.27 | −58 |
| 1.3 | 20 mg/kg compound 2 per day | 1.99 | −33 |
| 1.3 | 30 mg/kg compound 2 per day | 1.27 | −56 |

2) MRL-lpr/lpr mice (MRL/1) as SLE model

These animals spontaneously develop SLE. The MRL/1 mice have antibodies against nuclear constituents, hypergammaglobulins and circulating immune complexes. Death is normally caused by glomerulonephritis.

Experiment 2.1

This tested the effects of compound 1 on the development of SLE in male and female MRL/1 mice. Once the animals had reached 9 weeks of age they were divided into groups (n=20) and the treatment with the substance was started. Each animal received oral administration of 1 ml which contained in each case the amount of active compound indicated in Experiment 2.1, plus CMC in a concentration of 100 mg/l.

Untreated MRL/1 mice (positive control)
MRL/1 mice 5 mg/kg compound 1 per day
MRL/1 mice 20 mg/kg compound 1 per day
MRL/1 mice 28 mg/kg compound 1 per day
MRL/1 mice 35 mg/kg compound 1 per day
untreated NMRI mice (negative control)

a) Proteinuria

Figure 4:
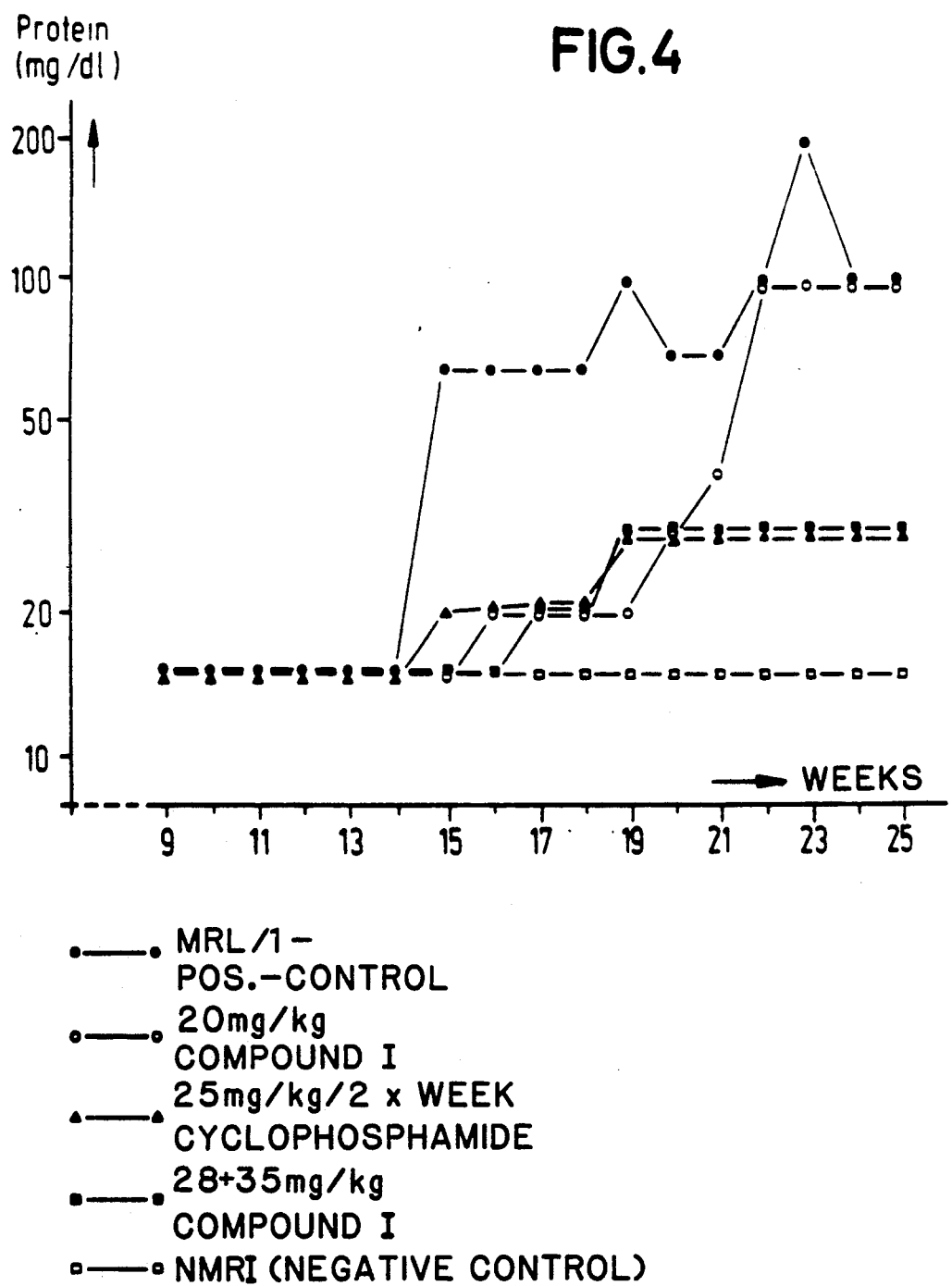
FIG. 4. Test results for female animals for protein excreted in the urine.

The protein excreted in the urine was measured as described under 1a). The results for female animals are shown in FIG. 4; the results for male animals were similar.

b) Titers of antibodies against double-stranded DNA (ds-DNA)

A feature of SLE is the presence of antibodies against nuclear constituents. The anti-ds-DNA antibodies of the IgG class are SLE-specific and are used for diagnosis. Once the animals had reached 35 weeks of age they were exsanguinated and the serum antibody titers were determined using a ELISA method [Enzyme-Linked Immunosorbent Assay; Kávai et al., J. Immunol. Meth. 48, 169–175 (1982); Pisetsky et al., J. Immunol. Methods 74, 217–227 (1984)]. The results are summarized in Table 3.

TABLE 3

| Substance | Titer (mean) | Range |
| --- | --- | --- |
| Untreated | 8145 | 3200–12800 |
| 5 mg/kg compound 1 per day | 8533 | 3200–12800 |
| 20 mg/kg compound 1 per day | 3844 | 1600–6400 |
| 28 mg/kg compound 1 per day | 1000 | 400–3200 |
| 35 mg/kg compound 1 per day | 470 | 50–2400 |
| Untreated +NMRI mice below | 100 | — |

±) NMRI = Naval Medical Research Institute c) Ability of T-lymphocytes to proliferate

Figure 5:
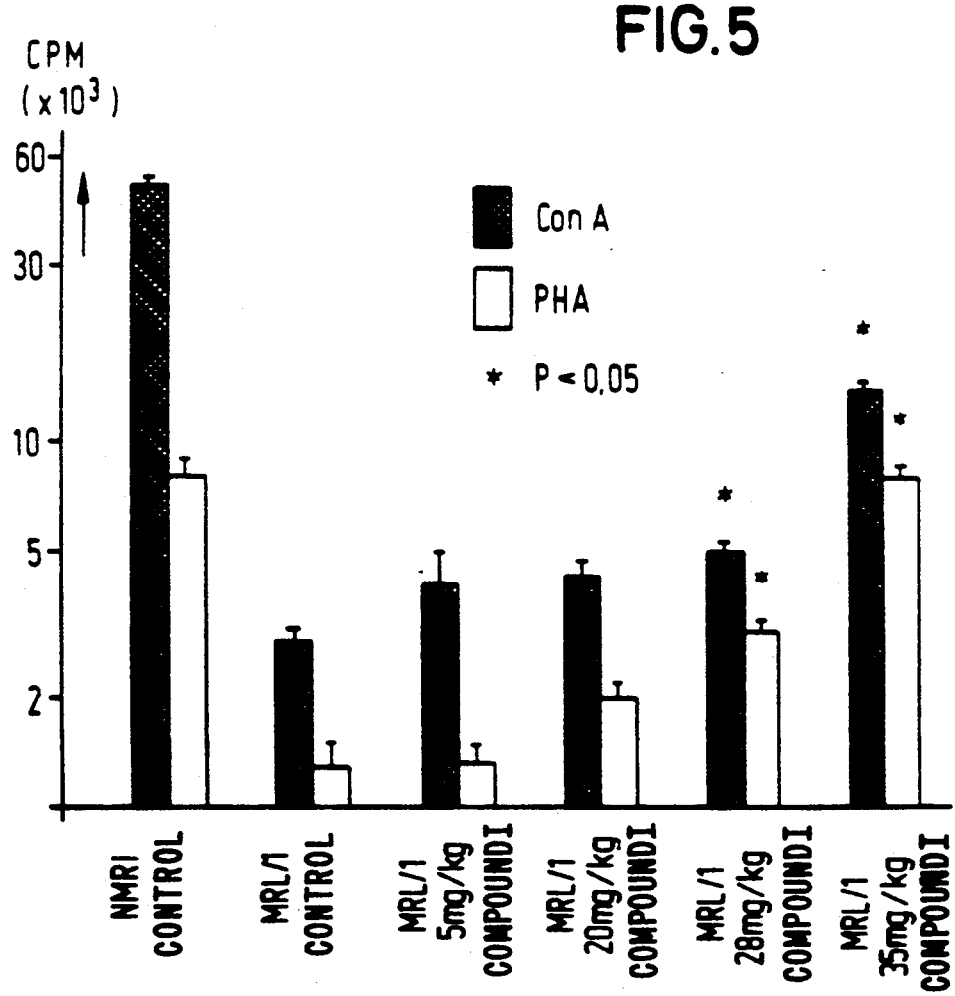
FIG. 5. The results of this Figure show that compound 1 effects a dose dependent improvement in the proliferation of T-lymphocytes stimulated by phytohemaglutinin (PHA) and concanavalin A (ConA).

Although there is massive proliferation of T-lymphocyte subclasses in MRL/1 mice, the proliferation by mitogens is reduced. It is assumed that this abnormal T-cell function makes a fundamental contribution to the etiology of the autoimmune disease in MRL/1 mice. Therapeutic regeneration of this diminished T-cell function would be beneficial. The spleen was removed under sterile conditions and treated as described by BARTLETT and SCHLEYERBACH [Int. J. Immunopharmacol. 7, 7–18 (1985)]. The results in FIG. 5 show that compound 1 effects a dose-dependent improvement in the proliferation of T-lymphocytes stimulated by phytohemagglutinin (PHA) and concanavalin A (ConA). The PHA-induced proliferation is in fact equal to that of lymphocytes from non-autoimmune NMRI mice.

The results of the abovementioned tests show that compounds 1 and 2 inhibit the development of cGvH diseases and SLE in mice.

These substances result in 1) prevention of the development of glomerulonephritis in both diseases; this has been shown by the diminution in the protein excreted in the urine and by histological tests on the kidneys;
2) a reduction in the anti-ds-DNA antibody titer;
3) a decrease in the GvH index;
4) a dose-dependent improvement in the diminished proliferation of T-lymphocytes.

Compounds 1 and 2 have advantages compared with immunosuppressants such as cyclophosphamide or glucocorticoids, since they do not cause general suppression of the immune system and, in fact, allow regeneration of the diminished T-cell function. It is all the more surprising that they very effectively combat chronic GvH diseases and SLE.

Compounds 1 and 2 can be administered either alone, where appropriate in the form of microcapsules, or mixed with customary physiologically tolerated excipients, diluents and/or ingredients. The agents can be administered orally, rectally, intravenously or parenterally, oral or rectal administration being preferred. Examples of suitable solid or liquid pharmaceutical presentations are granules, powders, tablets, coated tablets, capsules, suppositories, syrups, emulsions, suspensions, aerosols, drops or injectable solutions presented in ampules, this also including the dry ampule as a special presentation, as well as products with protracted release of active compound, in whose preparation use is customarily made of auxiliaries such as excipients, disintegrants, binders, coating agents, swelling agents, lubricants, flavorings, sweeteners, buffers, antioxidants and/or solubilizers. Examples of auxiliaries which are frequently used are magnesium or calcium carbonate, calcium phosphates, titanium dioxide, mannitol, lactose and other sugars, talc, lactalbumin, gelatin, starch, vitamins, cellulose and its derivatives, animal and vegetable oils, polyethylene glycols, and physiologically acceptable solvents such as sterile water, alcohols, glycerol and other polyhydric alcohols.

The pharmaceutical products are preferably prepared and administered in dosage units, each unit containing as active ingredient a defined dose of compound 1 and/or 2. This dose can be from 10 to 200 mg, but preferably 50 to 100 mg, for solid dosage units, such as tablets, capsules and suppositories, 1 to 30 mg, preferably 5 to 10 mg, for injection solutions presented in ampules (intravenous), especially those based on compound 2 or a salt thereof, and 50 to 300 mg, preferably 100 to 200 mg, for rectal administration.

In humans, daily doses of 50 to 200 mg of active compound on oral administration, of 10 to 30 mg on intravenous administration and of 100 to 300 mg on rectal administration are indicated for the treatment of an adult patient. However, in certain circumstances higher or lower daily doses may be advisable. The daily dose may be administered either as one dose in the form of a single dosage unit or as several smaller dosage units, as well as by administration of several divided doses at defined intervals.

Another use of the compounds comprises combination with other suitable active compounds, for example antiuricopathics, platelet aggregation inhibitors, analgesics and steroidal or non-steroidal antiinflammatory agents.

We claim:

1. A method of treating systemic lupus erythematosus which comprises administering to a recipient an effective amount of a pharmaceutical composition containing as an active ingredient at least one compound of the formulae 1 or 2

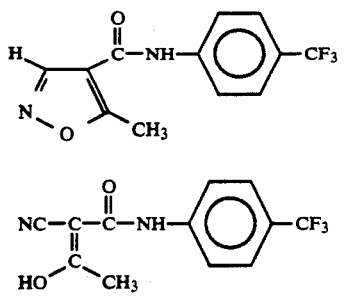

the latter being present per se or in the form of a physiologically tolerable salt.

2. A method according to claim 1, wherein the composition is present in a form which can be orally administered.

3. A method according to claim 1, wherein the composition is present in a form which can be rectally administered.

4. A method according to claim 1, wherein the composition is present in the form of an injectable solution and contains as an essential ingredient a compound of the formula 2 per se or in the form of a physiologically tolerable salt.

5. A method according to claim 1, wherein the dosage unit is in a form which can be orally administered and contains from 10 to 200 mg of at least one of the compounds 1 and 2, the latter being present per se or in the form of a physiologically tolerable salt.

6. A method according to claim 1, wherein the dosage unit is in a form which can be orally administered and contains from 50 to 100 mg of at least one of the compounds 1 and 2, the latter being present per se or in the form of a physiologically tolerable salt.

7. A method according to claim 1, wherein the dosage unit is in the form of an injectable solution containing from 1 to 30 mg of compound 2 per se or in the form of a physiologically tolerable salt.

8. A method according to claim 1, wherein the dosage unit is in a form which can be rectally administered which contains at least one of the compounds 1 and 2 in an amount of from 50 to 300 mg, compound 2 being present per se or in the form of a physiologically tolerable salt.

9. A method according to claim 1, wherein the dosage unit is in a form which can be rectally administered which contains at least one of the compounds 1 and 2 in an amount of from 100 to 200 mg, compound 2 being present per se or in the form of a physiologically tolerable salt.

10. A method as claimed in claim 1, wherein there is administered to a human recipient a daily dose in the range from 50 to 200 mg of active ingredient by oral administration, in the range from 10 to 30 mg by injection or in the range from 100 to 300 mg by rectal administration.

* * * * *